United States Patent [19]
Tadros et al.

[11] Patent Number: 6,121,033
[45] Date of Patent: Sep. 19, 2000

[54] DEGRADABLE POLYESTERS, A MIXED CULTURE OF MICROORGANISMS FOR DEGRADING THESE POLYESTERS, AND METHODS FOR MAKING THESE SUBSTANCES

[75] Inventors: Raef M. Tadros; Delmar C. Timm, both of Lincoln, Nebr.

[73] Assignee: The Board of Regents of the University of Nebraska, Lincoln, Nebr.

[21] Appl. No.: 09/358,348

[22] Filed: Jul. 21, 1999

Related U.S. Application Data

[62] Division of application No. 09/204,338, Dec. 2, 1998, Pat. No. 5,990,266.
[60] Provisional application No. 60/067,514, Dec. 4, 1997.

[51] Int. Cl.[7] .............................. C12N 9/20; C12N 1/00
[52] U.S. Cl. .............................. 435/198; 435/42; 435/43; 435/183; 435/187; 435/243; 435/252.4; 435/253.3; 435/254.3; 435/254.5; 435/254.9; 435/261; 435/262
[58] Field of Search ............................ 435/42, 43, 183, 435/187, 198, 243, 252.4, 253.3, 254.3, 254.5, 254.9, 261, 262

[56] References Cited

U.S. PATENT DOCUMENTS

| | | | |
|---|---|---|---|
| 4,873,194 | 10/1989 | Sawamura et al. | 435/198 |
| 5,204,251 | 4/1993 | Kyotani et al. | 435/134 |
| 5,219,753 | 6/1993 | Berka et al. | 435/252.3 |
| 5,246,848 | 9/1993 | Holmes | 435/198 |
| 5,429,942 | 7/1995 | Kock et al. | 435/134 |
| 5,529,917 | 6/1996 | Andreoli et al. | 435/198 |
| 5,606,007 | 2/1997 | Sakashita et al. . | |
| 5,756,650 | 5/1998 | Kawamonzen et al. . | |
| 5,830,735 | 11/1998 | Andreoli et al. | 435/198 |
| 5,929,017 | 7/1999 | Gormsen et al. | 510/392 |
| 5,976,855 | 11/1999 | Svendsen et al. | 435/198 |
| 5,985,795 | 11/1999 | Suganuma | 504/121 |
| 5,990,266 | 11/1999 | Tadros et al. | 528/288 |

OTHER PUBLICATIONS

Tokiwa et al., "Synthesis of Copolyamide–Esters and Some Aspects Involved in Their Hydrolysis by Lipase," *Journal of Applied Polymer Science,* vol. 24, 1701–1711, 1979.

Wang et al., "Fermentation and Enxyme Technology," *John Wiley & Sons,* pp. 57–97, 1979.

Ward, Owen P., "Fermentation Biotechnology," *Open University Press,* 1989.

Whitesides et al., "Enzymes as Catalysts in Synthetic Organic Chemistry," *Angewandte Chem. Int. Ed. Engl.,* vol. 24, pp. 617–718, 1985.

Fields et al., "Microbial Degradation of Polyesters: Polycaprolactone Degraded by *P. pullulans*," *Journal of Applied Polymer Science,* vol. 18, pp. 3571–3579, 1974.

Flory, Paul J., "A Comparison of Esterification and Ester Interchange Kinetics," *Journal of the American Chemical Society,* vol. 62, pp. 2261–2264, 1940.

Flory, Paul J., "Kinetics of the Degration of Polyesters by Alcohols," *Journal of the American Chemical Society,* vol. 62, pp. 2255–2261, 1940.

(List continued on next page.)

*Primary Examiner*—Samuel A. Acquah
*Attorney, Agent, or Firm*—Shook, Hardy & Bacon LLP

[57] ABSTRACT

Degradable polyesters useful in packaging, packing, agricultural, biomedical, and other applications are made by reacting amine-protected glutamic acid with diols or epoxy compounds. The polyesters include a thermoplastic main chain aliphatic polyester, a thermoset heterochain polyester and a thermoset heterochain aromatic polyester. Each of these polyesters can be hydrolyzed into monomers using a biological catalyst such as the enzyme lipase. The thermoplastic main chain aliphatic polyester and the thermoset heterochain polyester can be degraded to respiratory gases and biomass with a mixed culture of *Rhizopus chinesis, Rhizopus delemar, Penecillium pinophilum, Aspergillus niger* and *Pseudomonas aeruginosa* microorganisms. This mixed culture of microorganisms can also be used to degrade other polyesters containing hydrolyzable backbone polyesters.

2 Claims, 3 Drawing Sheets

OTHER PUBLICATIONS

Flory, Paul. J., "Kinetics of Polyestification: A study of the Effects of molecular Weight and Viscosity on reaction Rate," *Journal of the American Chemical Society,* vol. 61, pp. 3334–3340, 1939.

Freedman et al., "Photodegradable Vinyl Plastics. I. Effect of N–Halogen Additives," *Journal of Applied Polymer Science,* vol. 20, pp. 463–274, 1976.

Gibson, David T., "Microbial Degradation of Aromatic Compounds," *Science,* vol. 161, pp. 1093–1097, 1968.

Graham, Neil B., "Polymeric Inserts and Implants for the Controlled Release of Drugs," *The British Polymer Journal,* vol. 10, pp. 260–266, 1978.

Guillet, J.E., "Photochemistry in Macromolecular Systems," *Naturwissenschaften,* vol. 59, pp. 503–509, 1972.

Harper et al., "Mechanism of the Benzophenone–Sensitized Photodegradation of Polypropylene," *Journal of Applied Polymer Science,* vol. 17, pp. 3503–3508, 1973.

Harper et al., "Sensitised Photodegration of Polypropylene," *Journal of Chemistry and Industry* (London), pp. 848–849, 1972.

Haysashi et al., "Prepartion and Properties of A–B–A Tri–Block Copolymer Membranes Consisting of N–Hydroxyalkyl L–glutamine as the A Component and L–Alanine as the B Component," *Polymer Journal,* vol. 17, pp. 1273–1280, 1985.

Heller, J., "Controlled Release of Biologically Active Compounds from Biorodible Polymers," *Biomaterials,* vol. 1, pp. 51–57, 1980.

Huang et al., "Biodegradable Polymers: Photolysis and Fungal Degradation of Poly(arylene Keto Esters)," *Journal of Applied Polymer Science,* vol. 25, pp. 1951–1960, 1980.

Itoh et al., "Hydrolysis of Polyesters by Lipases," *Nature,* vol. 270. pp. 76–80, 1977.

Jarrett et al., "Mechanism of the Biodegradation of Polycaprolactone," *Plenum press,* New York, N.Y., pp. 181–192, 1984.

Klausmeier, R.E., "The Effect of Extraneous Nutrients on the Biodeterioration of Plastics," *Society of Chemical Industry,* S.C.I. Monograph No. 23, pp. 232–243, 1966.

Kluyver et al., "Microbial Metabolism and Its Industrial Implications," *Chemistry and Industry,* pp. 136–145, 1952.

Li–Xia et al., "Synthesis and Microbial Degradation of Poly(2–methyl phenylene oxide)," *Journal of Applied Polymer Science,* vol. 48, pp. 1081–1087, 1993.

Özilgen, Mustafa, "Kinetics of Amino Acid Production by Over–Producer Mutant Microorganisms," *Enzyme Microbial Technology,* vol. 10, pp. 110–114, 1988.

Paetau et al., "Biodegradable Plastic Made from Soybean Products. 1. Effect of Preparation and Processing on mechanical Properties and Water Absorption," *Indian Engineering Chemical Research,* vol. 33, pp. 1821–1827, 1994.

Peppler, Henry J., "Microbial Technology," *Reinhold Publishing Corporation,* pp. 435–437, 1967.

Potts et al., "The Biodegradability of Synthetic Polymers," *Synoposium on Polymers and Ecological Problems,* Plenum Press, New York, pp. 61–80, 1973.

Pramanick et al., "Studies on Some Radical Transfer Reaction by Entrapping the Radicals as Polymer Endgroups," *Acta Polymerica,* vol 39, pp. 357–361, 1988.

Reed et al., "Biodegradable Polymers for Use in Surgery – Poly(glycolic)/Poly(lactic acid) Homo and Copolymers: 2. In Vitro Degradation," *Polymer,* vol. 22, pp. 494–498, 1981.

Schindler et al., "Biodegradable Elastomeric Polyesters," *Polymeric Reprints,* pp. vol. 23, 111–112, 1982.

Stare et al., "The Effect of Fumarate on Respiration," *Proc. Roy. Soc.,* pp. 338–357, 1936.

Tokiwa et al., "Hydrolysis of Polyesters by *Rhisopus delemar* Lipase," *Agricultural and Biological Chemistry,* vol. 42, pp. 1071–1072, 1978.

Tokiwa et al., "Purification and Some Properties of Polyethylene Adipate–degrading Enzyme Produced by *Penicillium* sp. Strain 14–3[#]," *Agricultural and Biological Chemistry,* vol. 41, pp, 265–274, 1977.

Annau, E. et al., "Uber die Bedeutung der Fumarsäure für die tierische Gewebsatmung," *Hoppe–Seyler's Zeitschrift f. physiol. Chemie.* vol. 236, pp. 1–31, 1935. We believe this reference relates to microorganisms.

Annau, E. et al., "Uber die Bedeutung der Fumarsäure für die tierische Gewebsatmung," *Hoppe–Seyler's Zeitschrift f. physiol. Chemie.,* vol. 244, pp. 105–116, 1936. We believe this reference relates to microorganisms.

Bergmann et al., "Uber ein all–gemeines Verfahren der Peptid–Synthese," *Ber. Deut. Chem. Ges.,* vol. 65, pp. 1992–1201, 1932. We believe this reference relates to microorganisms.

Lynen, von Feodor, "Zum Biologischen Abbau der Essigsäure," *Annalen der Chemie,* vol. 552, pp. 270–306, 1957. We believe this reference relates to microorganisms.

Lynen, von Feodor, "Zum Biologischen Abbau der Essigsäure," *Annalen der Chemie,* vol. 554, pp. 40–68, 1957. We believe this reference relates to microorganisms.

Albertsson et al., "Biodegradation and Test Methods for Environmental and Biomedical Applications of Polymers," *CRC Press Boca Raton, Fl.,* pp. 263–293, 1990.

Albertsson, Ann–Christine, "Biodegradation of Synthetic Polymers. II A Limited Microbial Conversion of $^{14}$C in Polyethylene to $^{14}CO_2$ by some Soil Fungi," Journal of Applied Polymer Science, vol. 22, pp. 34319–3433, 1978.

Albertsson et al., "Biodegradation of Synthetic Polymers. III. The Liberation of $^{14}CO_2$ by Molds like Fusarium redolens from $^{14}$C Labeled Polyerized High–Density Polyethylene," Journal of Applied Polymer Science, vol. 22, 3435–3447, 1978.

Anderson et al., "The Potential for Poly–α–Amino Acids as Biomaterials," *Journal of Biomedical Material Resource Symposium,* No. 5, Part 1, pp. 197–207, 1974.

Benedict et al., "Fungal Degradation of Polycaprolactones," *Journal of Applied Polymer Science,* vol. 28, pp. 327–334, 1983.

Benedict et al., "Polycaprolactone Degradation by Mixed and Pure Cultures of Bacteria and a Yeast," *Journal of Applied Polymer Science,* vol. 28, 335–342, 1983.

Cook et al., "Scanning Electron Microscopic Visualization of Biodegradation of Polycaprolactones by Fungi," *Journal of Polymer Science:* Polymer Letters edition, vol. 19, pp. 159–165, 1981.

DeMoss et al., "Quantitative Aspects of the Tricarboxylic Acid Cycle in Baker's Yeast," *Journal of Bacteriology,* vol. 74, pp. 445–451, 1957.

Dennenberg et al., "A New Biodegradable Plastic made from Starch Graft Poly(methyl Acrylate) Copolymer," *Journal of Applied Polymer Science,* vol. 22, pp. 459–464, 1978.

De Simone et al., "Synthesis, Characterization, and Degradation of Block Polyesteramides Containing Poly(L–Lactide) Segments," *Journal of Applied Polymer Science,* vol. 46, pp. 1813–1820, 1992.

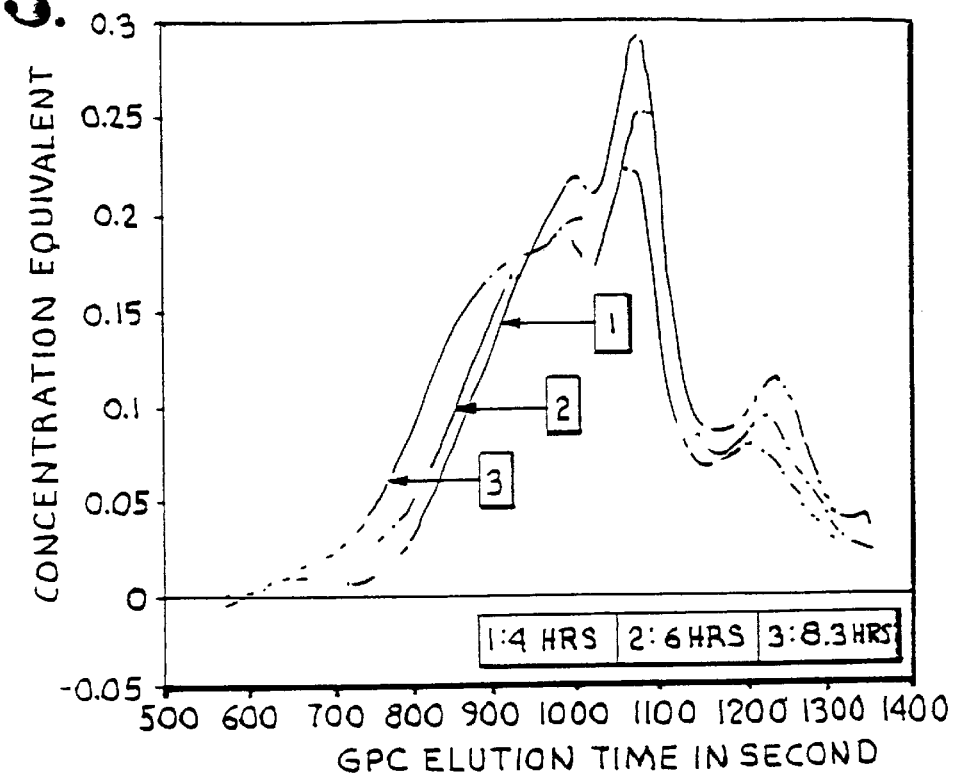
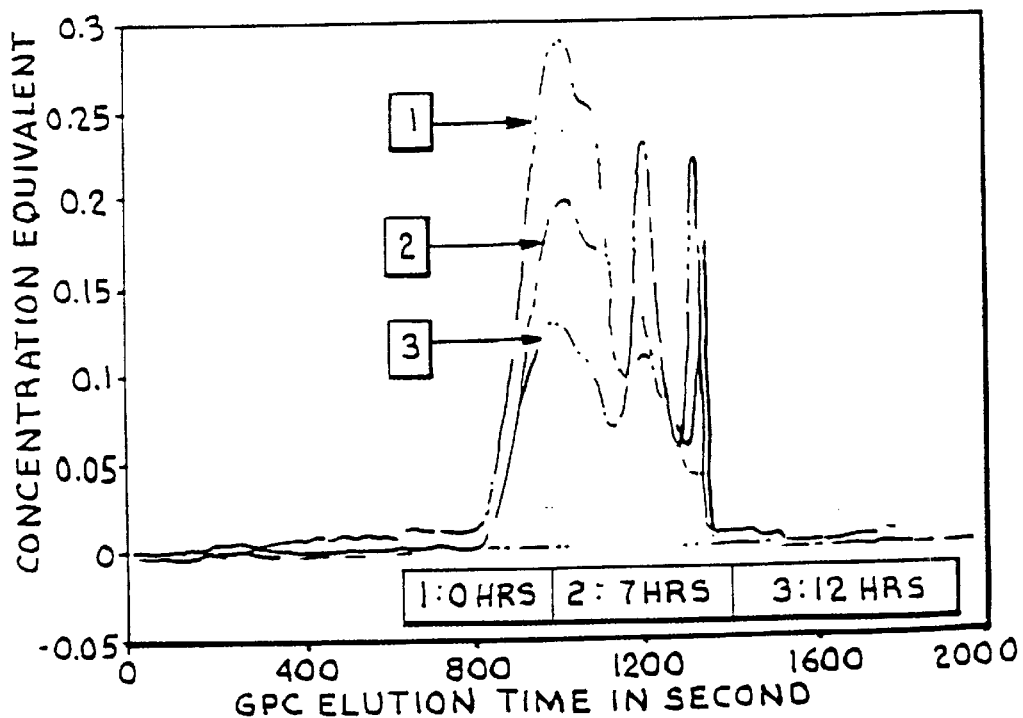

DEGRADABLE POLYESTERS, A MIXED CULTURE OF MICROORGANISMS FOR DEGRADING THESE POLYESTERS, AND METHODS FOR MAKING THESE SUBSTANCES

CROSS REFERENCE TO RELATED APPLICATIONS

This application claims the benefit of U.S. Provisional Application Ser. No. 60/067,514, filed Dec. 4, 1997 and is a division of U.S. patent application Ser. No. 09/204,338, filed Dec. 2, 1998 now U.S. Pat. No. 5,990,266.

STATEMENT REGARDING FEDERALLY-SPONSORED RESEARCH OR DEVELOPMENT

Not applicable.

BACKGROUND OF THE INVENTION

The present invention relates generally to polymeric materials and more particularly to polyesters, as well as methods for making and degrading polyesters. The invention also relates to a mixed culture of microorganisms that is able to degrade polymers containing a hydrolyzable backbone polyester and a method for making this mixed culture of microorganisms.

The majority of plastic materials available today are made from petroleum. Such petroleum-based plastics are difficult to degrade, biologically or otherwise. Because of the extensive use of petroleum-based plastics by both consumers and industry, a considerable amount of waste is created. This causes ecological problems because the waste is stored in landfills and other waste disposal systems and accumulates without degradation. Furthermore, petroleum is an expensive component of plastic.

Biodegradable polymers have been synthesized to provide alternatives to petroleum-based plastics. They are often synthesized from starch, sugar, natural fibers or other organic biodegradable components in varying compositions. However, such biodegradable polymers often lack desirable physical characteristics, and this limits their use to specific situations. Many biodegradable polymers are blended polymers or composite polymers and thus do not have uniform mechanical properties. Sill further, most known biodegradable polymers are aliphatic polyesters that have low softening points ($T_m$), which prevents their use as a material in a variety of fields.

In order to overcome the deficiencies found with conventional plastics and biodegradable polymers, a degradable polymer having enhanced strength and flexibility and a method for making such a degradable polymer are needed for a variety of applications. Still further, a polymer that is made from organic substances rather than petroleum-based compounds and a method for making this polymer are needed. In addition, certain formulations of this polymer should be biodegradable. A mixed culture of microorganisms that can be used to degrade the polymers of the present invention and other polymers and a method for making this mixed culture are also needed

SUMMARY OF THE INVENTION

It is an object of the present invention to provide degradable polymers having uniform mechanical properties and high softening points allowing them to replace petroleum-based plastics for various applications and a method for making such polymers in order to avoid the use of petroleum-based plastics and the waste generated by using such compounds.

It is a further object of the present invention to provide a mixed culture of microorganisms that can completely degrade different polyesters into respiratory gases and biomass and a method for making this mixed culture so that waste can be removed from the environment.

Another object of the present invention is to provide non-toxic degradable polymers and a method for making these polymers so that they can be used in the human body as drug-loaded matrices, surgical thread and surgical implants.

Still another object of the present invention is to provide biodegradable polymers having physical strength so that they can be used as a packaging material that can be disposed of by degradation.

According to the present invention, the foregoing and other objects are achieved by a thermoplastic main chain aliphatic polyester, a thermoset heterochain polyester, or a thermoset heterochain aromatic polyester. Each of these polymers are embodiments of the present invention that are made by reacting various organic compounds with blocked glutamic acid. The thermoplastic main chain aliphatic polyester is made by reacting diol with blocked glutamic acid. The thermoset heterochain and thermoset heterochain aromatic polyesters are formed by reacting an epoxy compound with blocked glutamic acid. All of these polyesters can be hydrolyzed into monomers when treated with certain biological catalysts such as the enzyme lipase. Furthermore, the thermoplastic main chain aliphatic polyester and the thermoset heterochain polyester can be completely degraded into respiratory gases and biomass using certain mixed cultures of microorganisms. One such mixed culture of microorganisms, which is an embodiment of the present invention, is comprised of the mixture of *Rhizopus chinesis, Rhizopus delemar, Penecillium pinophilum, Aspergillus niger* and *Pseudomonas aeruginosa*. The polyesters of the present invention may be used in medical applications, agricultural applications, packaging applications, packing applications, and any other applications where plastics are used.

Additional objects, advantages and novel features of the invention will be set forth in part in the description which follows, and in part will become apparent to those skilled in the art upon examination of the following, or may be learned from practice of the invention. The objects and advantages of the invention may be realized and attained by means of the instrumentalities and combinations particularly pointed out in the appended claims.

BRIEF DESCRIPTION OF THE DRAWINGS

The accompanying drawings form a part of this specification and are to be read in conjunction therewith.

FIG. 3 is a GPC graph of the thermoset heterochain aromatic polyester as it forms during the polymerization reaction.

FIG. 4 is a GPC graph of the thermoplastic main chain aliphatic polyester as it undergoes hydrolysis by lipase enzyme.

DETAILED DESCRIPTION OF THE PREFERRED EMBODIMENT

Figure 1:
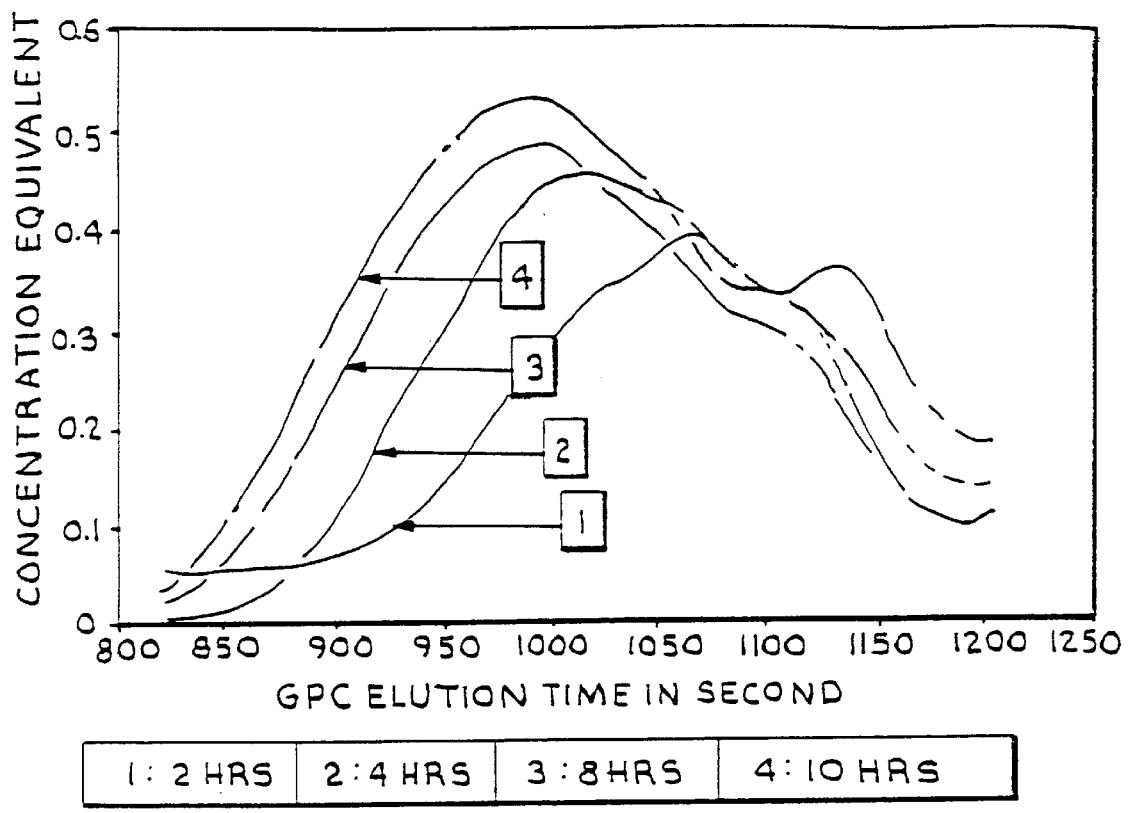
FIG. 1 is a Gel Permeation Chromatography (GPC) graph of the thermoplastic main chain aliphatic polyester as it forms during the polymerization reaction.

The polymers of the present invention are a thermoplastic main chain aliphatic polyester, a thermoset heterochain polyester, and a thermoset heterochain aromatic polyester. These polymers have structures which allow them to degrade. The polymer is hydrolyzed by the secretion of extracellular enzymes by microorganisms into low molecular weight compounds. These low molecular weight compounds can be introduced into the microbial cell for further degradation. All of these polyesters are formed by reacting amine-protected glutamic acid with various monomers. Still further, glutamic acid can be replaced by α-amino dicarboxyllic acids, such as aspartic acid, to produce polymers that are considered alternate embodiments of the present invention. The polymers that can be formed include polymers of various molecular weights, molecular structures and physical characteristics.

Glutamic acid is a biodegradable material according to the in vivo pathway of metabolism. For example, L-glutamic acid is an intermediate in the Krebs cycle. It is an inexpensive and abundant amino acid and exists in particularly high percentages in oilseed proteins, such as soybeans. In some genera of soybeans, about 60% of the seed is protein. Glutamic acid is a major component, about representing 18–22% of the amino acid content of major oilseed proteins. Glutamic acid also can be chemically synthesized or biologically produced (fermentation). Furthermore, there are many inexpensive commercially acceptable methods available for hydrolyzing and separating glutamic acid from the rest of the amino acids in the oilseed protein.

Using glutamic acid in polymerization reactions in its natural, unblocked form limits polymerization. When glutamic acid is heated with a monomer for polymerization, the glutamic acid tends to form cyclic compounds (mostly lactam) rather than linear molecular formations, and this inhibits the progress of polymerization. Therefore, in preparing the polymers of the present invention, it is first necessary to block the functional groups on the glutamic acid molecules, namely the amine groups, to prevent the formation of cyclic compounds such as lactam.

A number of different blocking agents can be used to block the amine group on the glutamic acid. These blocking agents include acyl-type protecting groups, urethan protecting groups, alkyl-type protecting groups, and arylidene-type protecting groups. Alternatively, rather than using blocking agents, the amine group can be protonated to block its functionality. Preferably, blocking of the glutamic acid is achieved by reacting it with carbobenzoxy chloride in an aqueous alkaline solution to form N-carbobenzoxy glutamic acid, which is commonly referred to as Z-glutamic acid. This reaction is inexpensive and provides about a 90% yield of Z-glutamic acid. Alternatively, Z-glutamic acid can be obtained from Aldrich Chemical Company, 1001 West Saint Paul Avenue, Milwaukee, Wis. 53233. Z-glutamic acid has the following structure:

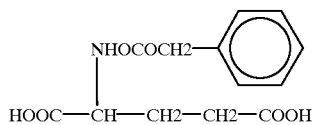

Once the blocked or amine-protected glutamic acid is formed or obtained, the polymers of the present invention can be created by reacting blocked glutamic acid with diol or epoxy compounds. More specifically, a diol, an aliphatic epoxy compound, or an aromatic epoxy compound are reacted with blocked glutamic acid in the presence of a catalyst to form a thermoplastic main chain aliphatic polyester, a thermoset heterochain polyester, or a thermoset heterochain aromatic polyester, respectively, the polyesters of the present invention. Each of the polyesters of the present invention is formed in a one-step reaction.

The polyester of the present invention is generally represented by the following structure, wherein X is an amine protecting group, Y is a diol or an epoxy compound that has been reacted with blocked glutamic acid, and n is an integer:

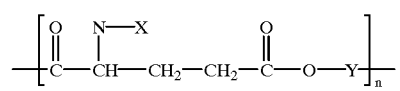

The thermoplastic main chain aliphatic polyester of the present invention may have the following structure when blocked glutamic acid is reacted with a diol, wherein R is an alkyl group, X is a protecting group, and n is an integer:

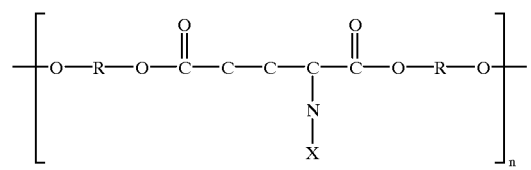

The thermoplastic main chain aliphatic polyester has the following structure when ethylene glycol is reacted with Z-glutamic acid, wherein n is an integer:

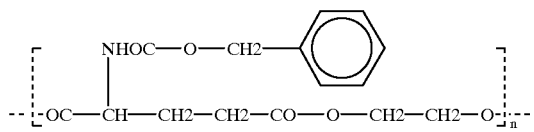

The thermoset heterochain polyester of the present invention and the thermoset heterochain aromatic polyester of the present invention may have one of the following structures (1), (2), or (3), when blocked glutamic acid is reacted with a diepoxy monomer, a triepoxy monomer, and a tetraepoxy monomer, respectively, wherein X is an amine protecting group, B is a branch node,

∽ is a polymer chain, and n is an integer:

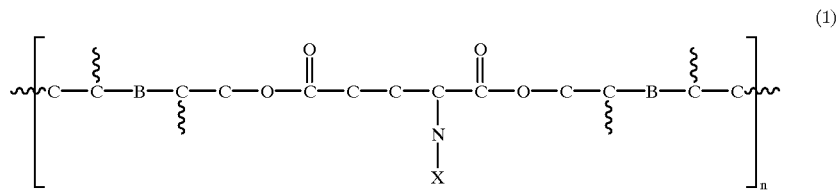

(1)

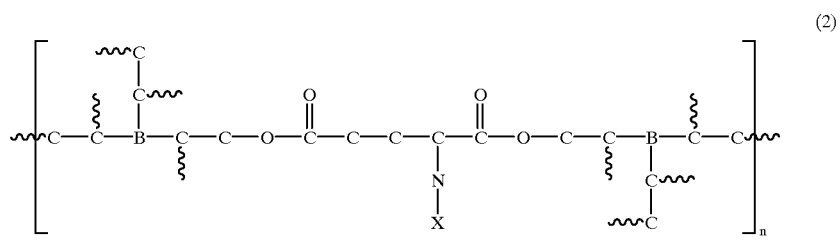

(2)

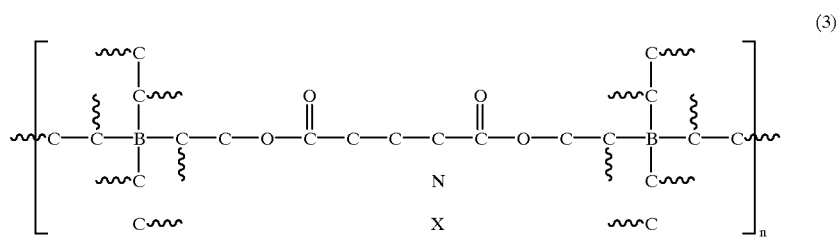

(3)

Indications of branch nodes and polymer chains in the above structures show that the polyester may have various structures depending upon the branching within the structure.

The thermoset heterochain polyester has the following structure when diglycidyl ether of 1,4Butanediol (BDE) is reacted with Z-glutamic acid, wherein n is an integer:

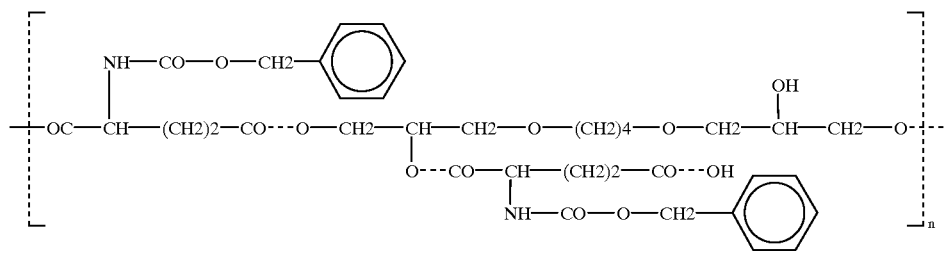

The thermoset heterochain aromatic polyester has the following structure when diglycidyl ether of bisphenol A (DGEBA) is reacted with Z-glutamic acid, wherein n is an integer.

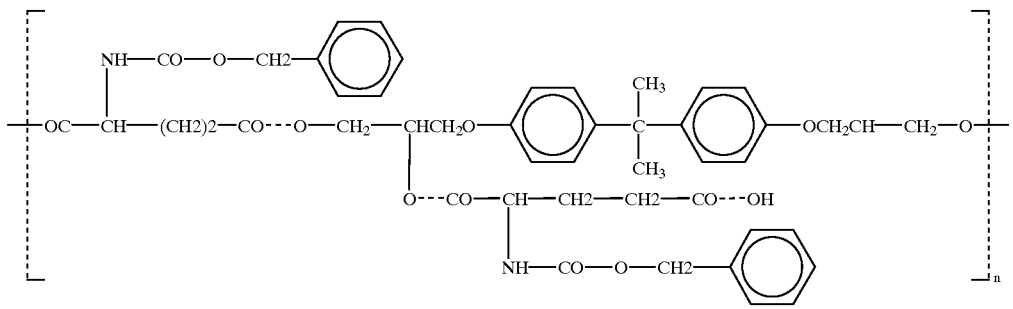

Examples of diols that may be used to form the thermoplastic main chain aliphatic polyester of the present invention include, but are not limited to, ethylene glycol, propylene glycol, 1,3-butanediol, 2,3-butanediol, 1,4-butanediol, 1,2-pentanediol, 1,4-pentanediol, 2,4-pentanediol, 1,5-pentanediol, 1,2-hexanediol, 1,5-hexanediol, 2,5-hexanediol, 1,6-hexanediol, and 1,7-heptanediol. Preferably, the diol has between about 2 and 14 carbon atoms. Most preferably, it has between about 2 and 8 carbon atoms. When diols having fewer carbon atoms are used in the polymerization reaction, more elastic polymers are formed.

Examples of aliphatic diepoxy components that may be used include, but are not limited to, 1,2,7,8-diepoxyoctane, neopentylglycol diglycidal ether, diglycidal ether of 1,4-butanediol, polyglycol diglycidal ether, and cycloaliphatic epoxies. The blocked glutamic acid can also react with triepoxy or tetraepoxy structures, which will lead to the formation of a polymer structure having a controlled amount of crosslinking.

Examples of diepoxy compounds that may be used to form the thermoset heterochain aromatic polyester of the present invention include, but are not limited to, a diglycidyl ether of bisphenol A, diglycidyl ether of 4,4'-biphenol, diglycidyl ether of 4,4'-hydroquinone, diglycidyl ether of 1,5-naphthalene diol, and diglycidyl ether of 2,7-naphthalene diol. The blocked glutamic acid also can be reacted with triepoxy structures, such as triglycidyl-p-aminophenol, or tetraepoxy structures, such as N,N,N',N'-tetraglycidyl-4,4'-diaminodiphenyl methane and tetraglycidyl ether of tetraphenolethane. The reaction of blocked glutamic acid with triepoxy and tetraepoxy structures will lead to a polymer structure having a controlled amount of crosslinking.

The polymerization reaction used to form the thermoplastic main chain aliphatic polyester, the thermoset heterochain polyester, and the thermoset heterochain aromatic polyester can proceed without the use of a catalyst so long as the reactants are heated and allowed to react for a sufficient amount of time. However, preferably, a catalyst is used in this polymerization reaction There are a variety of catalysts that may be used in this reaction, which include, but are not limited to, p-toluene sulfonic acid, sulfuric acid, titanium dioxide xhydrate, titanium tetrachloride, titanium tetrabutoxy, zinc chloride, and stannous oxide.

The blocked glutamic acid is combined with diol in a molar ratio between about 0.5:1 and 1:1.5; preferably, the molar ratio is about 1:1. The blocked glutamic acid is combined with the diepoxy compound in a molar ratio between about 0.5:1 and 2.5:1; preferably, the molar ratio is about 2:1. The blocked glutamic acid is combined with the triepoxy compound in a molar ratio between about 1:1 and 3.5:1; preferably, the molar ratio is about 3:1. The blocked glutamic acid is combined with the tetraepoxy compound in a molar ratio between about 1:1 and 4.5:1; preferably, the molar ratio is about 4:1. When excess diol or epoxy compound is present, dimers and trimers tend to form. If p-toluene sulfonic acid catalyst is used in this polymerization reaction, about 0.025 moles or less of the catalyst should be used per mole of blocked glutamic acid. Other molar ratios of catalyst to blocked glutamic acid may be preferred if a different catalyst is used.

After the diol or epoxy compound and the blocked glutamic acid are mixed, they are heated and a slow stream of inert gas, such as nitrogen or argon, is bubbled through the molten mixture. Preferably, this reaction occurs in vacuum conditions. This reaction should take place at about 90° C. or above for it to occur in a reasonable amount of time. Preferably, the component mixture is heated to between about 90 and 250° C. for about 16 to 24 hours if the diol is a reactant. Most preferably, the component mixture is heated to between about 140 and 170° C. if the diol is a reactant. Preferably, the polymerization reaction occurs at between about 90 and 170° C. if the epoxy compound is a reactant. Most preferably, the reaction occurs at between about 110 and 130° C. if the epoxy compound is a reactant. After heating the component mixture for at least about 2 hours at about 90° C. or above, a thermoplastic main chain aliphatic polyester will have formed and may be removed from the apparatus in which the reaction takes place. The resulting polymer should be cooled in a dissicator so as to avoid moisture contact, which may cause premature degradation. In addition to having a decreased reaction time at higher temperatures, the polymer resulting from a reaction at higher temperatures will have a higher molecular weight.

The thermoplastic main chain aliphatic polyester of the present invention has a number average molecular weight (Mn) between about 10,000 and 100,000. This polyester is considered a high quality resin, having good physical properties such as flexibility, impact resistance, the ability to entangle drugs within its matrix, and other desirable properties.

The thermoset heterochain polyester formed will have a higher molecular weight when the reactants are mixed for a longer time period or when the reaction occurs at a higher temperature. The thermoset heterochain polyester of the present invention is a somewhat elastic material. Crosslinks and bends in the structure of this polyester improve both its physical strength and its biodegradability. The extent of its elasticity is controlled by reactant ratios and reaction conditions. When an approximately equal molar ratio of blocked glutamic acid to epoxy compound is used, a more flexible and elastic polyester is created.

This thermoset heterochain aromatic polyester has a rigid crystalline structure. The bulky aromatic groups reduce carbon-carbon rotation, which stiffens the polyester. Thus, it has a stiff and brittle structure at room temperature.

Both the thermoset heterochain polyester and the thermoset heterochain aromatic polyester of the present invention can be considered high quality polymers depending upon how they are being used. Both these polymers have gel fractions ranging from about 99.9% to 75% and sol fractions ranging from about 0.1% to 25%. Usually, the gel fraction of these polymers ranges from about 50 to 60%. Materials having a gel fraction of close to 100% are hard, brittle and strong. Materials having lower gel fractions are softer, more ductile, more flexible and tend to swell.

The following are examples of the polyesters of the present invention and methods of making these polyesters. These examples are not meant in any way to limit the scope of this invention:

EXAMPLE 1

Method of Making a Thermoplastic Main Chain Aliphatic Polyester

Blocked glutamic acid and ethylene glycol were melt mixed together in a batch reactor under vacuum at 400 mmHg. Ethylene glycol has a low boiling point and was lost during the early stages of polymerization. At later stages of polymerization, ethylene glycol molecules became less volatile since they had reacted. P-toluene sulfonic acid catalyst was added to the mixture. The blocked glutamic acid and the ethylene glycol were added in quantities such that the molar ratio of blocked glutamic acid to ethylene glycol to p-toluene sulfonic acid was 1:1.08:0.01. The reaction was carried out at 110° C. and maintained at this temperature for the period of polymerization, which extended for 24 hours. The excess diol was stripped from the molten resin by vacuum. The reaction mixture was poured into a reaction bulb and heated in a liquid bath at a fixed temperature. A thermoplastic main chain aliphatic polyester of the present invention was obtained.

EXAMPLE 2

Method of Making a Thermoplastic Main Chain Aliphatic Polyester

Blocked glutamic acid and ethylene glycol were melt mixed together in a batch reactor under vacuum at 400 mmHg. Ethylene glycol has a low boiling point and was lost during the early stages of polymerization. At later stages of polymerization, ethylene glycol molecules became less volatile since they had reacted. P-toluene sulfonic acid catalyst was added to the mixture. The blocked glutamic acid and the ethylene glycol were added in quantities such that the molar ratio of blocked glutamic acid to ethylene glycol to p-toluene sulfonic acid was 1:1.08:0.01. The reaction was carried out at 170° C. and maintained at this temperature for the period of polymerization, which extended for 16 hours. The excess diol was stripped from the molten resin by vacuum. The reaction mixture was poured into a reaction bulb and heated in a liquid bath at a fixed temperature. A thermoplastic main chain aliphatic polyester of the present invention was obtained.

EXAMPLE 3

Method of Making a Thermoplastic Main Chain Aliphatic Polyester

Blocked glutamic acid and propylene glycol were melt mixed together in a batch reactor under vacuum at 400 mmHg. P-toluene sulfonic acid was added as a catalyst. The molar ratio between the blocked glutamic acid to the propylene glycol to the p-toluene sulfonic acid was 1:1.08:0.01. The reaction was carried out at 110° C. and maintained at this temperature for the period of polymerization, which extended for 22 hours. The excess diol was stripped from the molten resin by vacuum. The reaction mixture was poured into the reaction bulb and heated in a liquid bath at a fixed temperature. A thermoplastic main chain aliphatic polyester of the present invention was obtained.

EXAMPLE 4

Method of Making a Thermoplastic Main Chain Aliphatic Polyester

Blocked glutamic acid and 2,5-hexanediol are melt mixed together in a batch reactor under vacuum at 400 mmHg. P-toluene sulfonic acid is added as a catalyst. The molar ratio between the blocked glutamic acid to the 2,5-hexanediol to the p-toluene sulfonic acid is 1:1.08:0.015. The reaction is carried out at 170° C. and maintained at this temperature for the period of polymerization, which extends for 16 hours. The excess diol is stripped from the molten resin by vacuum. The reaction mixture is poured into the reaction bulb and heated in a liquid bath at a fixed temperature. A thermoplastic main chain aliphatic polyester of the present invention is obtained.

EXAMPLE 5

Method of Making a Thermoset Heterochain Polyester

A thermoset heterochain polyester was prepared by melt mixing equivalent amounts of blocked glutamic acid and diglycidal ether of 1,4 butanediol (BDE) in the presence of p-toluene sulfonic acid. These components were combined in a molar ratio of 1:1:0.02, respectively. The polymer mix was placed in a pre-heated oven at 110° C. After 15 minutes of heating, the temperature was raised gradually to the final temperature of 130° C., and the reaction was maintained at that temperature. The temperature was controlled to be within 0.5° C. difference of the set temperature for the period of polymerization, which extended for 8 hours.

EXAMPLE 6

Method of Making a Thermoset Heterochain Polyester

A thermoset heterochain polyester was prepared by melt mixing equivalent amounts of blocked glutamic acid and diglycidal ether of 1,4 butanediol (ODE) in the presence of p-toluene sulfonic acid These components were combined in a molar ratio of 1:1:0.02, respectively. The polymer mix was placed in a pre-heated oven at 110° C. After 15 minutes of heating, the temperature was raised gradually to the final temperature of 130° C., and the reaction was maintained at that temperature. The temperature was controlled to be within 0.5° C. difference of the set temperature for the period of polymerization, which extended for 8 hours.

EXAMPLE 7

Method of Making a Thermoset Heterochain Polyester

A thermoset heterochain polyester is prepared by melt mixing blocked glutamic acid and diglycidal ether of 1,4 butanediol (BDE) in the presence of p-toluene sulfonic acid. These components are combined in a molar ratio of 2:1:0.02, respectively. The polymer mix is placed in a pre-heated oven at 110° C. After 15 minutes of heating, the temperature is raised gradually to the final temperature of 130° C., and the reaction is maintained at that temperature. The temperature is controlled to be within 0.5° C. difference of the set temperature for the period of polymerization, which extends for 8 hours.

EXAMPLE 8

Method of Making a Thermoset Heterochain Aromatic Polyester

A thermoset heterochain aromatic polyester was prepared by melt mixing equivalent amounts of blocked glutamic acid and diglycidal ether of bisphenol A (DGEBA) in the presence of p-toluene sulfonic acid. These components were combined in a molar ratio of 1:1:0.02, respectively. The polymer mix was placed in a pre-heated oven at 110° C.

After 15 minutes of heating, the temperature was raised gradually to the final temperature of 120° C., and the reaction was maintained at that temperature. The temperature was controlled to be within 0.5° C. difference of the set temperature for the period of polymerization, which extended for 5 hours.

EXAMPLE 9

Method of Making a Thermoset Heterochain Aromatic Polyester

A thermoset heterochain aromatic polyester was prepared by melt mixing equivalent amounts of blocked glutamic acid and diglycidal ether of bisphenol A (DGEBA) in the presence of p-toluene sulfonic acid. These components were combined in a molar ratio of 1:1:0.02, respectively. The polymer mix was placed in a pre-heated oven at 110° C. After 15 minutes of heating, the temperature was raised gradually to the final temperature of 130° C., and the reaction was maintained at that temperature. The temperature was controlled to be within 0.5° C. difference of the set temperature for the period of polymerization, which extended for 5 hours.

EXAMPLE 10

Method of Making a Thermoset Heterochain Aromatic Polyester

A thermoset heterochain aromatic polyester is prepared by melt mixing blocked glutamic acid and diglycidal ether of bisphenol A (DGEBA) in the presence of p-toluene sulfonic acid. These components are combined in a molar ratio of 2:1:0.02, respectively. The polymer mix is placed in a pre-heated oven at 110° C. After 15 minutes of heating, the temperature is raised gradually to the final temperature of 130° C., and the reaction is maintained at that temperature. The temperature is controlled to be within 0.5° C. difference of the set temperature for the period of polymerization, which extends for 5 hours.

EXAMPLE 11

Method of Making a Thermoset Heterochain Aromatic Polyester

A thermoset heterochain aromatic polyester is prepared by melt mixing blocked glutamic acid and tetraglycidyl ether of tetraphenolethane with p-toluene sulfonic acid. These components are combined in a molar ratio of 4:1:0.01, respectively. The polymer mix is placed in a pre-heated oven at 110° C. After 15 minutes of heating, the temperature is raised gradually to the final temperature of 130° C., and the reaction is maintained at that temperature. The temperature is controlled to be within 0.5° C. difference of the set temperature for the period of polymerization, which extends for 10 hours.

Figure 2:
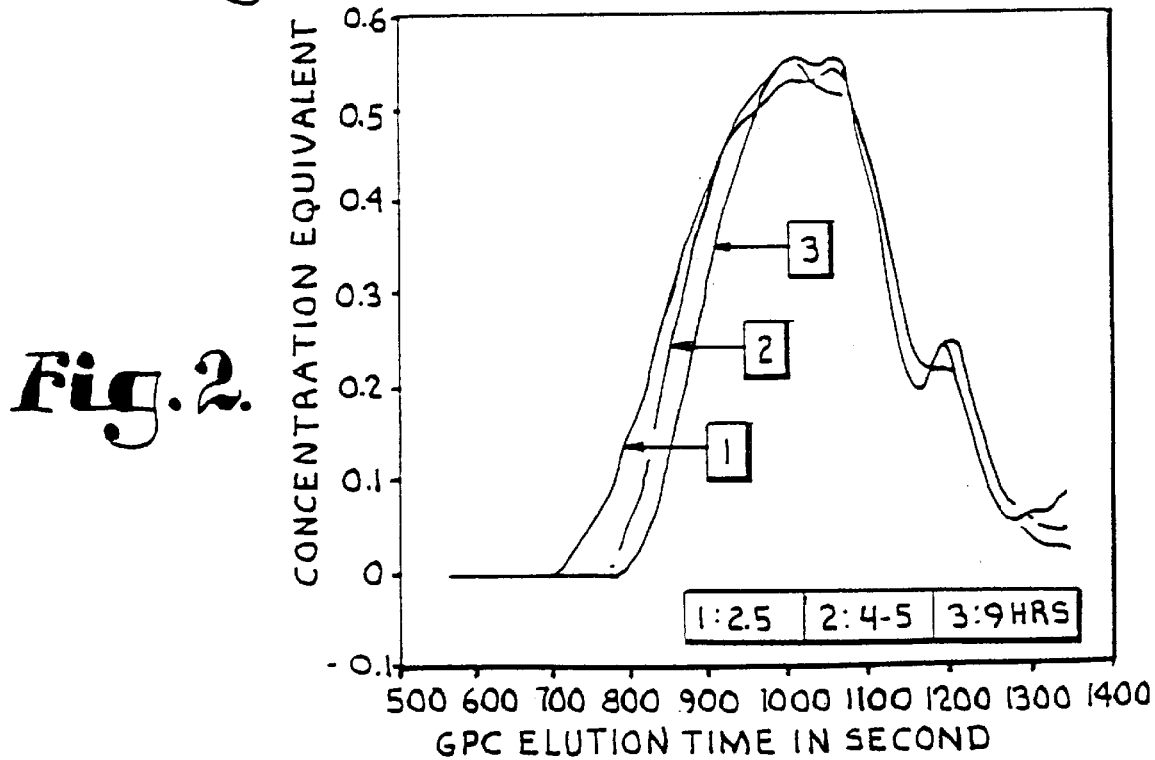
FIG. 2 is a GPC graph of the thermoset heterochain polyester as it forms during the polymerization reaction.

Gel Permeation Chromatography (GPC) is used to quantitate changes in molecular weight distribution of polymers during polymerization and degradation processes. The increase in molecular weight of the three novel polymers of the present invention during the polymerization reactions is shown in FIGS. 1–3.

Figure 5:
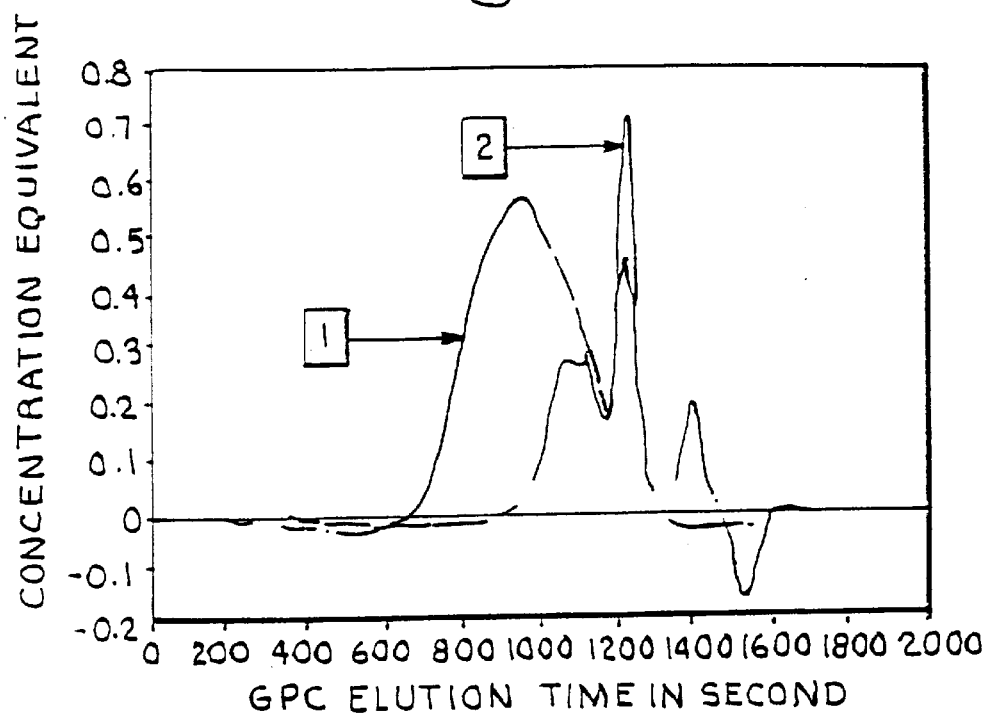
FIG. 5 is a GPC graph of the thermoset heterochain polyester as it undergoes hydrolysis by lipase enzyme.
Figure 6:
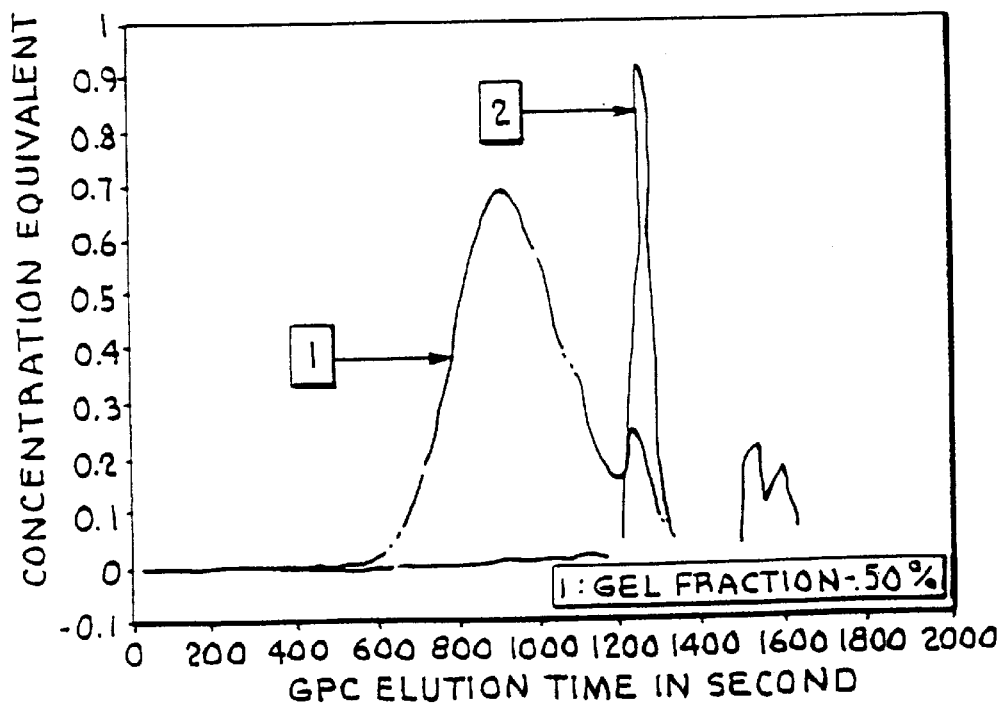
FIG. 6 is a GPC graph of the thermoset heterochain aromatic polyester as it undergoes hydrolysis by lipase enzyme.

Each of the polymer types of the present invention, namely, the thermoplastic main chain aliphatic polyester, the thermoset heterochain polyester, and the thermoset heterochain aromatic polyester, can be hydrolyzed into their monomeric units by many biological catalysts. An esterase enzyme, such as lipase, which is extracted from the microorganism *Rhizopus delemar* or other microorganisms, is one example of a biological catalyst that may be used to hydrolyze the polyesters. Another biological catalyst that can be used is hog liver esterase. The biological catalyst randomly splits the ester bonds of the polyester, hydrolyzing it into low molecular weight compounds. Hydrolysis into monomers is the first step of degradation. The decline in molecular weight of the three polymers of the present invention as they undergo hydrolysis is shown in FIGS. 4–6.

Another step of degradation involves treating these polymers with a mixed culture of microorganisms, which is designed to metabolize or break down the polymers' structures. In catabolic processes occurring in nature, such as the degradation of cellulose and lignin, biodegradation proceeds best using mixed populations of microorganisms and is restricted or incomplete when a pure culture or a single strain of microorganisms is used In the same way, mixed cultures were chosen to metabolize the polyesters of the present invention rather than a pure culture. Cellulose or lignin degradation may resemble the degradation of plastics in a general way but not with respect to enzymological details. Since differences among microorganisms always implies differences in enzymatic activities, in forming the mixed culture of microorganisms of the present invention, the mixed culture used to degrade cellulose or lignin was modified by incorporating fungal strains whose enzymatic capability related to the structure of the polyesters of the present invention. The microorganisms (mold and bacteria) chosen are known to produce specific enzymes. Furthermore, they are known to have a degradable effect on specific classes of polymers and are capable of metabolizing aromatic structures.

The mechanism of biodegradation is a composite effect of chemical reactions that proceed simultaneously on the polymer, accounting for the fact that a second species may be able to flourish after the first has started to wane. Most of the microbial reactions are sequential so that the end product of metabolism of a given substrate by one organism becomes the substrate for another organism. The mixed culture of microorganisms of the present invention is believed to metabolize the synthesized polymers of the present invention in the same approach.

The mixed culture of microorganisms of the present invention is comprised of *Rhizopus chinesis, Rhizopus delemar, Penecillium pinophilum, Aspergillus niger,* and *Pseudomonas aeruginosa.* Preferably, these microorganisms are combined in equal proportions. Other fungal strains have the capability of metabolizing the same polymer structure, and thus, one or more microorganisms may be substituted in the mixed culture. Different species from the same genus may be used in forming the mixed culture of microorganisms. For instance, *Penecillium brevicompactum, Penicillium funciculosun,* or *Penecillium cyclopium* may be added to the mixed culture or may be used as a substitute for *Penecillium pinophilum.* Still further, for example, *Aspergillus amstelodami, Aspergillus flavus, Aspergillus amstelodami,* or *Aspergillus versicolor* may be added to the mixed culture or may be used as a substitute for *Aspergillus niger.* Other Rhizopus and Pseudomonas species may be used in the mixed culture and may be especially effective in degrading polyesters with different chemical structures. The addition of one or more microorganisms should not have any effect on the degradability of the various polymers since the chosen mixed culture has a wide degradable effect over a variety of polyesters with different chemical structures.

The mold Rhizopus is capable of metabolizing different nutrient carbon sources, such as sugars, ethanol or acetic acid, when each is the only source of carbon available. The *Rhizopus delemar* lipase enzyme randomly splits ester bonds. It is extracted from Rhizopus species of microorganisms. Different Rhizopus species become a part of the mixed culture of the present invention. *Aspergillus niger* is effective in metabolizing different nutrient carbon sources. *Aspergillus niger, Pseudomonas aeruginosa,* and *Penicil-*

*lium pinophilum* are capable of metabolizing different polyesters. *Pseudomonas putida, pseudomonas cruciviae* and *nocardia restrictus* are effective in degrading aromatic structures. These microorganisms are representative of the microorganisms used in the mixed culture of the present invention.

The following is an example of a method for preparing a mixed culture of microorganisms. This example is not meant in any way to limit the scope of this invention.

EXAMPLE 12

A Method for Preparing a Mixed Culture of Microorganisms

The mixture of spores was prepared from separate cultures of microorganisms. Sabouraud dextrose dehydrated media (broth media) was used as a nutrient for the initial microbial growth. The cultivated broth media was prepared by dissolving 30 grams of the dehydrated broth media in one liter of distilled water. A volume of 50 ml of the dissolved media was poured into several 150 ml Erlenmeyer flasks. The prepared flasks were sterilized at 120° C. for 20 minutes. Each fungi used in the mixed culture was cultivated initially in one flask.

The lyophilized preparation of each test organism was inoculated into the prepared broth liquid media The prepared cultures were incubated at 30° C. in an incubator orbital shaker at 150 rounds per minute (rpm). After fifteen days of growth, 10 ml of the media containing the fungus growth was poured into 100 ml of distilled water and was shaken vigorously to liberate the spores. The media was filtered through a milk filter to separate hyphae from spores. The filtrate was centrifuged to separate the spores from the liquid media Repetitive suspension of the precipitate with distillate water and recentrifugation proceeded to remove any traces of nutrient media (carbon source) from the spores. The collected spores were diluted by 1 ml of the salt liquid media Spores were collected for each test organism. Equal volumes of the resulted spore suspension were mixed and about 1 ml of the fungus spores mixture were prepared to be used for inoculation. The bacteria were directly inoculated. Reserve stock of each microorganism was stored in the refrigerator. It should be renewed at least every four weeks and preferably in between 10 and 20 days.

The developed mixed culture of microorganisms of the present invention can degrade numerous polyesters, including the thermoplastic main chain aliphatic polyester of the present invention, the thermoset heterochain polyester of the present invention, polylactic acid (PLA), polycaprolactone (PCL), and polyglycolic acid (PGA), into biomass and respiratory gases. The biodegradation of the thermoplastic main chain aliphatic polyester and the thermoset heterochain polyester can proceed to completion.

The structure of these polymers is the essential element of their biodegradability, and the percentage of hydrolyzable ester bonds on the polymer affects biodegradation. The extent to which the thermoset heterochain polyester of the present invention is degradable relates to the extent of crosslinking in the polyester.

The biodegradable polyesters of the present invention, the thermoplastic main chain aliphatic polyester and the thermoset heterochain polyester, decompose into non-toxic compounds. The microorganisms can grow and utilize these polyesters as carbon sources for nutrition.

The following is an example of a method for degrading the polymers of the present invention using the mixed culture of microorganisms of the present invention. This example is not meant in any way to limit the scope of this invention.

EXAMPLE 13

A Method for Degrading Polymers Using a Mixed Culture of Microorganisms

In order to test the polymer toward microbial degradation, a fermenter from the submerged culture system was designed with suitable growth conditions. The degradation was estimated and modeled by quantifying the evolved $CO_2$ and the growing biomass. In this method, the test fungi consisted of a mixture of *Rhizopus chinesis, Rhizopus delemar, Penecillium pinophilum, Aspergillus niger,* and *Pseudomonas aeruginosa.*

The carbon content of the polymers was transferred into respiratory gases and biomass growth. The weight loss in the polymer sample is measured with time. Respiratory activity of the degrading microorganisms was followed by analyzing the inlet and outlet gases coming to and from the cultivator flask The inlet air stream was free of $CO_2$, for both the thermoplastic main chain aliphatic polyester and the thermoset heterochained polyester samples.

The thermoset heterochain aromatic polyester of the present invention resisted biological degradation when contacted by the mixed culture of microorganisms discussed above. It ether resisted degradation when *Pseudomonas cruciviae, Pseudomonas putida,* and *Corynebacterium resticta,* all three of which are capable of metabolizing aromatic structures, were added to the mixed culture. The thermoset heterochain aromatic polyester is a hard and brittle material due to the stiffness associated with the aromatic structure of the main chain. It appeared that the chemical structure of the thermoset heterochain aromatic polyester does not allow fungus adhesion followed by extracellular enzyme secretion, both of which are necessary for microbial degradation.

The polymers of the present invention may be used in consumer and industrial products for making an assortment of plastics including packaging and packing materials. They provide advantages over conventional materials because of their degradability. The polymers of the present invention also have characteristics that make them suitable for use as agricultural mulches and agricultural chemicals. Because both the thermoplastic main chain and thermoset heterochain polyesters are completely degradable into respiratory gases and biomass without having a toxic effect on the microbes in the mixed culture of microorganisms used to degrade them, it is reasonable to assume that the same results can be shown with other biological cells. Thus, the polymers of the present invention are ideally suited for use in biomedical applications such as drug-delivery systems and surgical implants, because these polyesters decompose into non-toxic compounds. If used as a drug-delivery matrix, these polymers can be loaded with pharmaceutical compounds and inserted into a patient whereupon the polymer would harmlessly degrade and release the drug in a sustained and controlled manner for a long period of time. These thermoplastic main chain aliphatic polyesters disclosed herein are similar in application to polylactic acid, a biodegradable polymer which is currently in commercial use as a time-release drug delivery matrix. The thermoset heterochain and thermoset heterochain aromatic polyesters of the present invention are similar in application to crosslinked polycaprolactone, another biodegradable polymer, which has shown potential for use in similar biomedical applications.

From the foregoing, it will be seen that this invention is one well adapted to attain all the ends and objects hereinabove set forth together with other advantages that are obvious and inherent to the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

We claim:

1. A mixed culture of microorganisms, comprising a mixture of:

*Rhizopus chinesis;*

*Rhizopus delemar;*

*Penecillium pinophilum;*

*Aspergillus niger;* and

*Pseudomonas aeruginosa.*

2. A method for making a mixed culture of microorganisms, comprising:

dissolving cultivated broth media in water;

cultivating microorganisms, namely, *Rhizopus chinesis, Rhizopus delemar, Penecillium pinophilum,* and *Aspergillus niger* in said broth media, wherein each microorganism is cultivated separately from the others;

filtering each of said microorganisms to separate hyphae from spores; and mixing said spores from said microorganisms to form a mixed culture of microorganisms.

* * * * *